United States Patent [19]

Southard

[11] Patent Number: 4,517,172

[45] Date of Patent: May 14, 1985

[54] PLAQUE DISCLOSING AGENT

[75] Inventor: George L. Southard, Fort Collins, Colo.

[73] Assignee: Vipont Laboratories, Inc., Fort Collins, Colo.

[21] Appl. No.: 566,916

[22] Filed: Dec. 29, 1983

[51] Int. Cl.³ .................... A61K 7/26; A61K 35/78
[52] U.S. Cl. ................................ 424/7.1; 424/49; 424/58; 514/195.1
[58] Field of Search ................ 424/7.1, 49, 58, 195

[56] References Cited

U.S. PATENT DOCUMENTS

| | | | |
|---|---|---|---|
| 209,331 | 10/1878 | Daniel | 424/195 |
| 2,344,830 | 3/1944 | Mohs | 424/195 |
| 3,309,274 | 3/1967 | Brilliant | 424/7.1 |
| 4,145,412 | 3/1979 | Ladanyi | 424/58 |
| 4,335,110 | 6/1982 | Collins | 424/58 |
| 4,406,881 | 9/1983 | Ladanyi | 424/49 |

FOREIGN PATENT DOCUMENTS

| | | |
|---|---|---|
| 888843 | 11/1981 | Belgium . |
| 2907406 | 9/1980 | Fed. Rep. of Germany . |
| 2042336 | 9/1980 | United Kingdom . |

OTHER PUBLICATIONS

Hocking—A Dictionary of Terms in Pharmacognosy, Chas. C. Thomas, Springfield, Ill. (1959), pp. 199–200, "*Sanguinaria canadensis*".

Windholz et al., Merck Index, 9th Ed. (1976), Merck & Co., Rahway, N.J., #8111 "Sanguinaria", #8112 Sanguinarine, #2007 Chelerythrine, #7684 Protupine.

Steinmetz, Codex Vegetabilis (1957), Amsterdam, Neth., #1018 "*Sanguinaria canadensis*".

Ladanyi (Vipont) (I) C.A. 96 #129814e (1982) of Belgium, No. 888,843, Nov. 19, 1981 (U.S. Ser. No. 24,604, Mar. 28, 1979).

Ladanyi (Vipont) (II) C.A. 93 #245285v (1980) of Ger. Off. No. 2,907,401, Sep. 4, 1980.

Ladanyi (Vipont) (III) C.A. 94 #214607t (1981) of Brit. U.K. Pat. Appl. No. 2,042,336, Sep. 24, 1980.

*Primary Examiner*—Shep K. Rose
*Attorney, Agent, or Firm*—Eric P. Schellin

[57] ABSTRACT

Salts of sanguinarine, either pure salts or a mixture of said salts precipitated from extracts of plants selected from the group consisting of *Sanguinaria canadensis, Macleya cordata, Corydalis sevctvozii, C. ledebouni, Chelidonium majus,* and mixtures thereon, are effective agents for disclosing plaque in the oral cavity under long wavelength ultraviolet light.

8 Claims, No Drawings

PLAQUE DISCLOSING AGENT

BACKGROUND OF THE INVENTION

This invention relates to novel disclosing agents for use in the improvement of oral hygiene practices.

Dental plaque is a well-organized structure which forms on tooth surfaces and restorations. It consists mainly of bacteria surrounded by a matrix derived primarily from saliva and the bacteria themselves. Plaque differs from other soft tooth deposits such as material alba and food debris in that it has a definite architecture and cannot be flushed away by rinsing with water.

It is well established that dental plaque plays a major role in the etiology of periodontal diseases and caries. Although the exact manner in which plaque contributes to these disease states is not known at present, it is appreciated that effective and thorough removal of these deposits is absolutely essential for control program be established as part of the treatment plan for every dental patient. For this program to be effective the patient must be motivated to carry out thorough daily plaque control techniques. Motivation can be achieved, however, only by establishing goals that are meaningful and attainable by the patient. Experience has shown that most patients would not be sufficiently motivated to practice good oral hygiene if they were simply told that plaque is a bacterial colony growing on their teeth, and that plaque produces gingival disease and caries and must be removed daily. However, the entire concept of what plaque is and what it does to tissue can be made vital and important to the patient by visualization, whereby every patient is shown has plaque in situ and under the phase contrast of a microscope. The patient may also observe the diseased gingival areas and their juxtaposition to the places of plaque accumulations. These visual demonstrations serve two main purposes. First, it shows the patient that he does indeed have these dangerous bacterial deposits called plaque on his teeth. Secondly, in the microscopic visualization, he sees that those innocent looking masses are composed to millions of living bacteria of differing shapes. Experience has shown that the technique of visualization of plaque generates in patients a true interest in plaque and an obvious and apparent concern for its prompt removal.

Recent evidence has shown that plaque has a great destructive potential and, under varying conditions, can cause gingivitis and periodontitis, produce dental caries, or form into calculus. It has also been established that plaque accumulation which is allowed to develop without removal in many cases may cause gingivitis within one to twenty one days. There is also recent evidence indicating that plaque with all of its components may be capable of producing an allergic response in adjacent soft tissues.

This rather substantial potential destructiveness has given rise to the increased attention and the resultant recent attempts to educate the public in its control. Generally, this control has adopted an approach of oral lavage and focused on the tasks such as brushing, stimulating, massaging, rinsing spraying, and the like. However, while these techniques are effective for the removal of food debris and similar foreign matter, they are not very effective for removal of plaque. Plaque formation is transparent and is therefore not readily visible, particularly to one who is not skilled in its detection, and most often its removal occurs mainly by accident during oral lavage.

In order to increase the effectiveness of plaque detection and removal there has been a recent introduction into the marketplace of staining compositions or so-called disclosing compositions. these disclosing compositions contain coloring agents or dyes which are designed to be absorbed by the plaque to make the plaque visually distinguishable from the remainder of the oral cavity. The active staining ingredient in most of these commercially available disclosing compositions is generally iodine or several organic dyes which serve as the primary diagnostic agent.

Organic dyes have been almost universally adopted for use in the commercially available disclosing compositions because of their higher degree of effectiveness. However, in almost all of these cases these dyes have a highly unpalatable and objectionable taste which is not effectively masked by any known flavoring agent or sweetener.

In order to obviate the need of disclosing solutions as a diagnostic device, there has been a recent introduction in the marketplace of fluorescent light detection systems. These types of light detection systems rely upon compositions which are introducable into the oral cavity and contain an ingredient which is fluorescent when activated by a proper light source. It is contended that the fluorescent ingredient or dye is absorbable by the plaque and that the fluorescent dye will only fluoresce on the areas containing plaque formation when excited by this proper light source. However, in most cases the dye fluoresces at the same color as the enamel and, therefore, the plaque is not readily distinguishable. Furthermore, the purchase cost for these systems and the difficulty encountered in using these systems generally have militated against their widespread use.

SUMMARY OF THE INVENTION

It has been found that sanguinarine salts disclose plaque equally as well as two standard disclosing agents, erythrosine and fluorescein. However, sanguinarine has been found to be retained on the plaque deposits for a significantly longer time than the standard disclosing agents, and sanguinarine is known to have antimicrobial properties.

The longer retention time for sanguinarine on plaque deposits makes it an ideal disclosant for use in dental offices, by allowing dental cleansings during the disclosure period while maintaining an antibacterial action of sanguinarine is particularly important in the case of ultrasonic scaling, where aeralization of mouth deposits is an occupational hazard to dentists and dental hygienists. Compositions containing sanguinarine as a disclosing agent can also be used by consumers for self-disclosure of plaque in the home to aid in oral hygiene.

The sanguinarine may be incorporated into a disclosing composition in a variety of ways. The most common method is to incorporate the sanguinarine into a mouthwash composition, which is used to rinse the mouth prior to examining for plaque deposits. Alternatively, the sanguinarine may be incorporated in a test cracker or other chewable food such as candy or gum which will aid in diagnosing plaque. Sanguinarine can also be incorporated into toothpaste to enable the patient to observe the care with which he is brushing.

In formulating preparations suitable for the above, one may include, if desired, one or more additives which are useful for other purposes. For example, brightening agents, solvents spreading, or wetting agents, etc., may be used for various purposes. Almost any known mouthwash, toothpaste, tooth powder, or other formulation useful for diagnostic or therapeutic treatment of external body surfaces and of the oral cavity may be used.

Sanguinarine chloride was compared to two standard disclosing dyes, erythrosine and sodium fluorescein. At weekly intervals healthy volunteers under went a 12–24 hour, no oral hygiene period. Subjects then used one of the following: erythrosine, sodium fluorescein, or sanguinarine chloride. Subjects rinsed two times with 15 ml. of the rinse, while the erythrosine and sodium fluorescein were used according to customary practice. Color was evaluated under ambient light after erythrosine, under Plak light for sodium fluorescein, and under longwave UV fluorescent light for sanguinarine. The color was scored for location, amount, and area.

All agents colored soft dental deposits at gingival margins and at the dorsal surface of the tongue. Erythrosine also stained the gingivae and other soft tissues, whereas sodium fluorescein and sanguinarine did not. Mean values of plaque were measured for all disclosants. Table shows that the sanguinarine chloride mouthwash disclosed plaque effectively, and that the disclosure lasted significantly longer than for the other two disclosing dyes.

TABLE I

| | Visual Assessment | |
|---|---|---|
| | Mean Plaque Area Score | |
| Active Agent | Baseline | 1 Hour later |
| Erythrosine | 2.86 + 0.43 | 2.18 + 0.5 |
| Sodium Fluorescein | 2.84 + 0.22 | 1.74 + 0.45 |
| Sanguinarine Chloride | 2.87 + 0.23 | 2.86 + 0.26 |

Quantitative evaluation of sanguinarine in plaque and saliva by means of high performance liquid chromatography demonstrated levels in plaque much higher in vitro minimum inhibitory concentrations, as shown in Table II.

TABLE II

| In Vivo Plaque Retention of Sanguinarine (ug/g of Wet Plaque) | | | | | | |
|---|---|---|---|---|---|---|
| | Sample time, Minutes | | | | | |
| Subject | 15 | 30 | 45 | 60 | 90 | 120 |
| 1 | 26 | — | 22 | — | 26 | — |
| 1A | 110 | — | 27 | — | 30 | — |
| 2 | 29 | — | 27 | — | 31 | — |
| 2A | 79 | — | 56 | — | 46 | — |
| 3 | 111 | — | 37 | — | 36 | — |
| 3A | 160 | — | 34 | — | 36 | — |
| 4 | — | 96 | — | 56 | 51 | — |
| 5 | — | 46 | — | 46 | 46 | 27 |

Levels of sanguinarine in saliva, as shown in Table III, were high enough to exert an anti-glycolitic effect on saliva. This would indicate that the retention of sanguinarine in plaque may be responsible for its clinical effectiveness in plaque assays, and that plaque may serve as a reservoir for sanguinarine.

TABLE III

| In Vivo Saliva Retention of Sanguinarine (ug/ml of Saliva) | | | |
|---|---|---|---|
| | Sample time, Minutes | | |
| Subject | 15 | 45 | 60 |
| 6 | 1.13 | 0.92 | 0.45 |
| 7 | 1.47 | 0.75 | 0.60 |
| 26 | 0.96 | 0.79 | 1.00 |
| 20 | 0.80 | 0.57 | 0.42 |

TABLE III-continued

| In Vivo Saliva Retention of Sanguinarine (ug/ml of Saliva) | | | |
|---|---|---|---|
| | Sample time, Minutes | | |
| Subject | 15 | 45 | 60 |
| 27 | 0.90 | 0.90 | 0.80 |
| 21 | 0.47 | 0.17 | 0.22 |
| 28 | 2.63 | 1.25 | 0.54 |
| 22 | 0.50 | 0.29 | 0.18 |
| 24 | 1.05 | 0.85 | 0.80 |

DESCRIPTION OF THE PREFERRED EMBODIMENTS

Sanguinarine chloride and its related salts have been found to be useful in controlling dental plaque, as disclosed in copending application Ser. No. 468,751, filed Feb. 22, 1983, by the instant inventor, now abandoned, which disclosure is incorporated herein by reference. The sanguinarine salts which have been found to be useful in plaque disclosing agents include the chloride, the nitrate, and the sulfate salts, as well as all mixtures of said salts which might be precipitated or purified from the extracts of *Sanguinaria canadensis* and other members of the Papaveracease family.

The sanguinarine salts which have been found useful as plaque disclosing agents include sanguinarine salts, either as pure isolates or in mixtures of benzophenanthridine salts such as sanguinarine nitrate, sanguinarine sulfate, Sanguiritin, and all other mixtures which might be precipitated from the extracts of *Sanguinaria canadensis, Madleaya cordate, Carydalis sevctvozii, C. ledebouni, Chelidonium majusm* and other members of the Papaveracease.

EXAMPLE I

An oral rinse was formulated for use as a disclosing agent. The rinse contained the following ingredients:
Ethyl alcohol: 10.00%
Sanguinarine extract: 0.03%
Citric acid: 0.03%
Flavoring (oil of cinnamon): 0.25
Polysorbate 80: 0.60
Glycerine: 3.46
Deionized water: 85.23
Poloxamer 40%: 0.10
Sodium saccharine: 0.10
Zinc chloride: 0.20

This was the oral rinse used for the tests described in Tables I, II, and III.

EXAMPLE II

An oral rinse is formulated for use as a disclosing agent substituting 0.10% of mixed salts precipitated from *Sanguinaria canadensis* for the sanguinarine chloride above. This oral rinse, when used in a quantity of about 15 ml. for 15 seconds in the mouth have acceptable plaque disclosure in the mouth under long wavelength ultraviolet light (approximately 365 mm.)

Oral rinses for use as plaque disclosing agents can incorporate from 0.001 to 1% pure sanguinarine salt (chloride, nitrate, sulfate), and from about 0.003 to about 3% mixed benzophenanthridine alkaloids (34% sanguinarine by weight).

The oral rinse compositions which have been found useful for the practice of the present invention generally comprise a water/ethyl alcohol solution and, optionally, other ingredients such as flavors, sweeteners, and humectants. The rinse may also contain sudsing agents to aid in penetration of the plaque. The sudsing agent is generally present in amounts of about 0 to 12% y weight, with optional flavoring and coloring agents.

Suitable sudsing agents are those which are reasonably stable and form suds throughout a wide pH range, i.e., nonsoap nonionic, cationic, and amphoteric organic synthetic detergents.

The nonionic synthetic detergents which can be used with the oral rinse compositions of the present invention may be broadly defined as compounds produced by the condensation of a hydrophilic alkylene oxide group with an organic hydrophobic compound which may be aliphatic or aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Cationic synthetic degergent useful in the mouthwash compositions of the present invention can be broadly defined as quaternary ammonium compounds having one long alkyl chain containing from about 8 to about 18 carbon atoms, such as lauryltrimethylammonium chloride, cetyl pyridinium chloride, cetyl trimethylammonium bromide di-isobutylphenoxyethyldimethylbenzylammonium chloride, coconutalkyltrimethylammonium nitrite, cety pyridinium fluoride, and the like.

The amphoteric synthetic detergents useful in the present invention can be broadly described as derivatives of aliphatic secondary and tertiary amines in which the aliphatic radical can be straight or branched and wherein one of the aliphatic substituents contains from about 8 to about 18 carbon atoms and one contains an anionic water solubilizing group, such as carboxylate, sulfonate, sulfate, phosphate, or phosphonate.

The oral rinse for use as a disclosing agent can also contain flavoring agents such as wintergreen oil (methyl salicylate), oil of peppermint, oil of sassafras, and oil of anise. Flavoring agents may be present at levels of from about 0.01% to about 2% by weight.

The oral rinse can also contain sweetening agents, such as saccharin, dextrose, and aspartame, levulose. The sweetening agents are used at levels of from about 0.05% to about 2% by weight.

The disclosing compositions of the present invention may also be incorporated in pastes or powders that are topically applied, or in form of chewable foodstuffs that can be chewed b the patient to apply the disclosing composition.

EXAMPLE III

A toothpaste is made by mixing together the following ingredients in the indicated proportions:
Insoluble sodium metaphosphate: 26.60%
Dicalcium phosphate: 26.60
Gum: 1.40
Flavoring: 1.60
Sodium lauryl sulfate: 1.10
Glycerol (40.7%) and water (1.0%): 41.70
Sanguinarine sulfate: 1.00

The patient's teeth are brushed with this paste, and then exposed to longwave UV light. The plaque on the teeth stands out in bold relief as compared to the adjacent clean and healthy areas.

EXAMPLE IV

A toothpowder is made by mixing together the following ingredients, in the indicated proportions:
Microcrystalline aluminum hydroxide: 91.25%
Aluminum hydroxide (325 mesh): 5.00
Flavoring matter: 0.60
Saccharin, soluble: 0.25
Sodium fluoride: 0.10
Sodium lauryl sulfoacetate: 2.30
Sanguinarine chloride: 0.50

The sanguinarine salts can also be incorporated in chewable foods such as gums, gels, candies, or crackers which can be chewed by a patient to apply the sanguinarine salts to the teeth to disclose plaque.

What is claimed is:

1. A method for visualizing plaque formation in the oral cavity and rendering such plaque formation visible to the naked eye under long wavelength ultraviolet light by applying to the oral cavity a sanguinarine salt selected from the group consisting of sanguinarine chloride, sanguinarine nitrate, sanguinarine sulfate, and a mixture of said salts precipitated from extracts of plants selected from the group consisting of *Sanguinaria canadensis, Macleaya cordata, Corydalis sevctvozii, C. ledebouni, Chelidonium majus,* and mixtures thereof.

2. The method of claim 1 wherein the sanguinarine salt is sanguinarine chloride.

3. The method of claim 1 wherein the sanguinarine salt is contained in an oral rinse.

4. The method of claim 3 wherein the sanguinarine salt is sanguinarine chloride.

5. The method of claim 3 wherein the sanguinarine salt is a mixture of benzophenanthridine salts extracted from *Sanguinaria canadensis.*

6. The method of claim 1 wherein the sanguinarine salt is applied in the form of a toothpaste.

7. The method of claim 6 wherein the sanguinarine salt is sanguinarine chloride.

8. The method of claim 1 wherein the sanguinarine salt is applied in the form of a toothpowder.

* * * * *